US006234969B1

(12) United States Patent
Chaintreuil et al.

(10) Patent No.: US 6,234,969 B1
(45) Date of Patent: May 22, 2001

(54) BONE SONOMETRY, DENSITOMETRY AND IMAGING

(75) Inventors: Jean Stephane Chaintreuil, Paris (FR); Danny Lambrechts, Rijmenam (BE); David A. Davis, Sudbury; Lorraine Schuft, Stow, both of MA (US); Daval Liuhar, Vienna (AT)

(73) Assignee: Hologic, Inc., Bedford, MA (US)

( * ) Notice: Subject to any disclaimer, the term of this patent is extended or adjusted under 35 U.S.C. 154(b) by 0 days.

(21) Appl. No.: 09/241,973

(22) Filed: Feb. 1, 1999

(51) Int. Cl.[7] ........................................ A61B 8/02
(52) U.S. Cl. ........................................... 600/449
(58) Field of Search .................... 600/449, 438; 73/597, 599; 364/413.25; 356/243

(56) References Cited

U.S. PATENT DOCUMENTS

| | | | |
|---|---|---|---|
| 4,568,184 | * | 2/1986 | Krantz et al. .................... 356/243 |
| 4,913,157 | * | 4/1990 | Pratt, Jr. et al. ................. 600/449 |
| 5,134,999 | * | 8/1992 | Osipov ............................. 600/449 |
| 5,349,959 | * | 9/1994 | Wiener et al. .................... 600/449 |
| 5,755,228 | | 5/1998 | Wilson et al. . |
| 5,778,045 | | 7/1998 | von Stetten et al. . |
| 5,785,041 | | 7/1998 | Weinstein et al. . |
| 5,806,520 | * | 9/1998 | Berger et al. ..................... 600/449 |

OTHER PUBLICATIONS

"Sahara Clinical Bone Sonometer" printed for Hologic, Inc. under the designation B–130 U.S. Oct. 1997.

* cited by examiner

*Primary Examiner*—Marvin M. Lateef
*Assistant Examiner*—Ali M. Imam
(74) *Attorney, Agent, or Firm*—Cooper & Dunham LLP

(57) ABSTRACT

A bone sonometer or densitometer or small C-arm having a card reader that requires a charge to a card in order to carry out a patient examination but not procedures that may be similar or even identical to a patient examination from the machine's point of view, such as calibration procedures involving the use of phantoms. The card can be rejuvenated locally or from a remote location, via a communication link. Instead of a card, remote per-use authorization can be provided upon making a charge. In the case of a small C-arm, the card can keep track of radiation dosage to a user associated therewith.

23 Claims, 3 Drawing Sheets

BONE SONOMETRY, DENSITOMETRY AND IMAGING

FIELD

This patent specification pertains to the field of medical diagnostic equipment and processes and, more particularly, to the field of bone assessment and other equipment-based diagnostic processes.

BACKGROUND

Osteoporosis is a common disease associated with low bone mineral density (BMD). Bone is lost naturally with age, and this tends to be accelerated after menopause. People with low bone density often do not realize they are at risk of osteoporosis until a fracture occurs, by which stage bone may have been irreplaceably lost from the skeleton. There are a number or risk factors for osteoporosis, but the most important is thought to be low BMD. Early recognition of bone loss is important in the identification of individuals at risk of osteoporosis, particularly in view of the increasing availability of preventative and therapeutic interventions that can reduce the impact of bone loss and prevent the increase of fracture risk due to bones becoming more fragile.

Until recently, bone mineral density was measured mainly through the use of x-ray based technologies such as dual energy x-ray absorptiometry (DXA or DEXA) and, to a lesser extent, quantitative computed tomography (QCT). Other techniques were used earlier, such as single photon absorptiometry, but are no longer widely used. DXA and QCT techniques have many desirable characteristics, such as high sensitivity and the ability to accurately predict fracture risk, but use ionizing radiation and relatively expensive equipment. More recently, ultrasound has become available for bone assessment. Using quantitative ultrasound (QUS), it is possible to measure or estimate ultrasonic characteristics of bone and thereby estimate bone mineral density and assess the risk of fracture. Ultrasound also has been shown to be reliable in estimating bone mineral density and predicting the risk of fracture, and has the desirable characteristics of not involving ionizing radiation and using lower cost equipment. In addition, there is a class of x-ray based medical devices called small C-arm fluoroscopes, or simply small C-arms, that typically are used for both surgery and diagnosis of extremities, but can be provided with the additional capability of making bone assessment measurements.

As an example of commercially available products of this type, Hologic, Inc. of Bedford, Mass. offers a line of DXA equipment under the trade names ACCLAIM and QDR and model designations such as 4500 and 1000, an ultrasound bone sonometer under the trade name Sahara, and a small C-arm under the trade name Fluoroscan followed by model designations. See, e.g., U.S. Pat. No. 5,778,045 pertaining to x-ray bone densitometry, U.S. Pat. Nos. 5,755,228 and 5,785,041 and U.S. patent application Ser. No. 08/477,580 pertaining to ultrasound bone sonometry, and U.S. patent application Ser. No. 08/794,615 pertaining to small C-arm x-ray devices. See, also, a brochure entitled "SAHARA Clinical Bone Sonometer" printed for Hologic, Inc. Under the designation B-130 U.S. (10/97). Said patents and applications and said brochure are hereby incorporated by reference in this patent specification as though fully set forth herein.

In non-analogous fields of technology and business, consumers have long used cards such as credit and debit cards and smart cards to pay for goods and services, and individuals have used access cards to gain admittance to controlled facilities. While often the purchaser hands the card over to a sales person who inserts it in a card reader, there are cases in which the purchaser has direct access to the card reader, e.g., at some gas stations.

However, patients typically do not operate bone sonometry or densitometry or small C-arm equipment, and no patient-provided cards are known to be involved in turning such diagnostic equipment on to carry out some, but perhaps not all, of the procedures such equipment carries out. Nor are the owners or operators of bone sonometers or densitometers known to be required to use cards to make the equipment carry out examinations. Indeed, charging a card to turn on a bone sonometer or densitometer for an examination may not appear practical at first blush, and may be counter-intuitive, because some procedures do not directly produce revenue to the owner or operator. For example, a bone sonometer or densitometer may require periodic calibration examinations, e.g., once a day, in which the equipment measures a calibration object (phantom) rather than a patient or makes a measurement through a medium other than a patient's body or extremity. Quality control procedures and service and maintenance procedures can also be similar or even identical to patient examinations from the machine's point of view, but also are not directly revenue-generating for the machine's user. Similar, though not necessarily identical, considerations can apply to DXA bone densitometers and small C-arm equipment.

SUMMARY

This patent specification discloses, as an exemplary and non-limiting embodiment, a system in which an ultrasound bone sonometer requires a charge to a card in order to carry out a patient examination but not in order to carry out procedures such as calibration, testing, quality control, maintenance or service procedures that can otherwise be similar or even identical to a patent examination from the equipment's viewpoint. Typically, the health professional or other operator of the bone sonometer controls the card rather than the patient. The health professional inserts the card as needed in a card reader integrated physically and electronically with the bone sonometer. The card need not be unique to a patient and need not be unique even to the operator of the bone assessment equipment, although it can be. The card can be prepaid, allowing a certain number of patient examination before its value is used up, or can allow some forms of credit. The card can be a single-use card, so that a new card is issued as needed, or it can be of the type that can be rejuvenated by changing its information content. Instead of, or in addition to the use of a card, on-line charging can be carried out though a telecommunication link between the diagnostic equipment or its operator and a remote charging operation.

With the system disclosed in detail in this patent specification, a health care facility can benefit from having the full use of a bone sonometer or densitometer without having to buy one and take the risk that the revenue it produces may not justify the purchase price or finance charges. Instead, the health care facility can have the convenience of a bone densitometer on its premises for the relatively small investment in a card, if the card is of the prepaid type, or for no significant investment if the card is of the type that allows for some form of credit or on-line charging via a telecommunication link. If the bone sonometer or densitometer is of the type that requires no special room or installation, such as the aforementioned Sahara ultrasound bone sonometer which is portable and light, less than 25 lbs., and uses household-type current outlets, the health care facility can start patient examinations without having to make any significant incremental investment in the new equipment. In accordance with the exemplary system disclosed in this patent specification, the effect is that the health care facility pays for using the bone sonometer or densitometer when the use is directly revenue-generating and there is a net revenue when the charge to the card is subtracted from the fee charged to or for the patient, but the facility incurs no charge when the bone sonometer or densitometer is put to a use that may be otherwise necessary but is not directly revenue: generating, even though the equipment may be carrying a procedure otherwise similar or even indistinguishable from a patient examination from the machine's point of view.

The card preferably is a smart card that contains processing and memory circuitry for validation, keeping track of charges and other records and, if desired, rejuvenation information. In other embodiments, more conventional magnetic-stripe cards can be used to keep and update similar information. The cards can be issued by or for the supplier of the bone sonometer or densitometer or by a third party. If rejuvenation is desired, it can be carried out by or for the card issuer or a third party to whom the card is physically returned, or it can be carried out via a communication link such as an Internet connection.

In addition, similar or special cards can be issued to service personnel for use in quality control, testing, maintaining, servicing, or upgrading bone sonometers or densitometers.

A card reader is physically and electronically incorporated in the bone sonometer or densitometer, e.g., by enclosing it in the equipment's housing, with only a card slot accessible from the outside, powering the card reader by the equipment's power supply, and electronically connecting it to an internal information carrying bus, e.g., a bus that also allows connecting the bone sonometer or densitometer to an external computer or to a communication link.

In the case of a DXA bone densitometer, the card reader can be similarly incorporated in the machine, and can similarly control operations to allow patient examinations if a card is charged but to allow other procedures without such a charge. If desired, different charges can be made to the card for different types of patient examinations, e.g., hip, whole body, extremity, morphometry, etc. The different charges can differ in dollar (or other unit of currency) amount, or in some other way.

In the case of a small C-arm, a card reader can be similarly incorporated in the equipment, and can allow patient fluoroscopy or bone densitometry upon charging a card but allow other procedures without such a charge. Moreover, C-arm users such as surgeons or other health professionals who work with or at the C-arm can have individual cards providing additional functions, such as keeping track of x-ray dosage by recording the time the person has been exposed to radiation from the machine and from similar machines on which the card is used and, if desired, keeping track of additional information. Because several individuals may use the same small C-arm at different times, or the same individual may use different small C-arms at different times, such use of the card can provide a more accurate way of ensuring that an individual stays within x-ray exposure dosage limits than relying on time records of a particular C-arm or on radiation dosage badges.

DETAILED DESCRIPTION OF EXEMPLARY EMBODIMENTS

Figure 1:
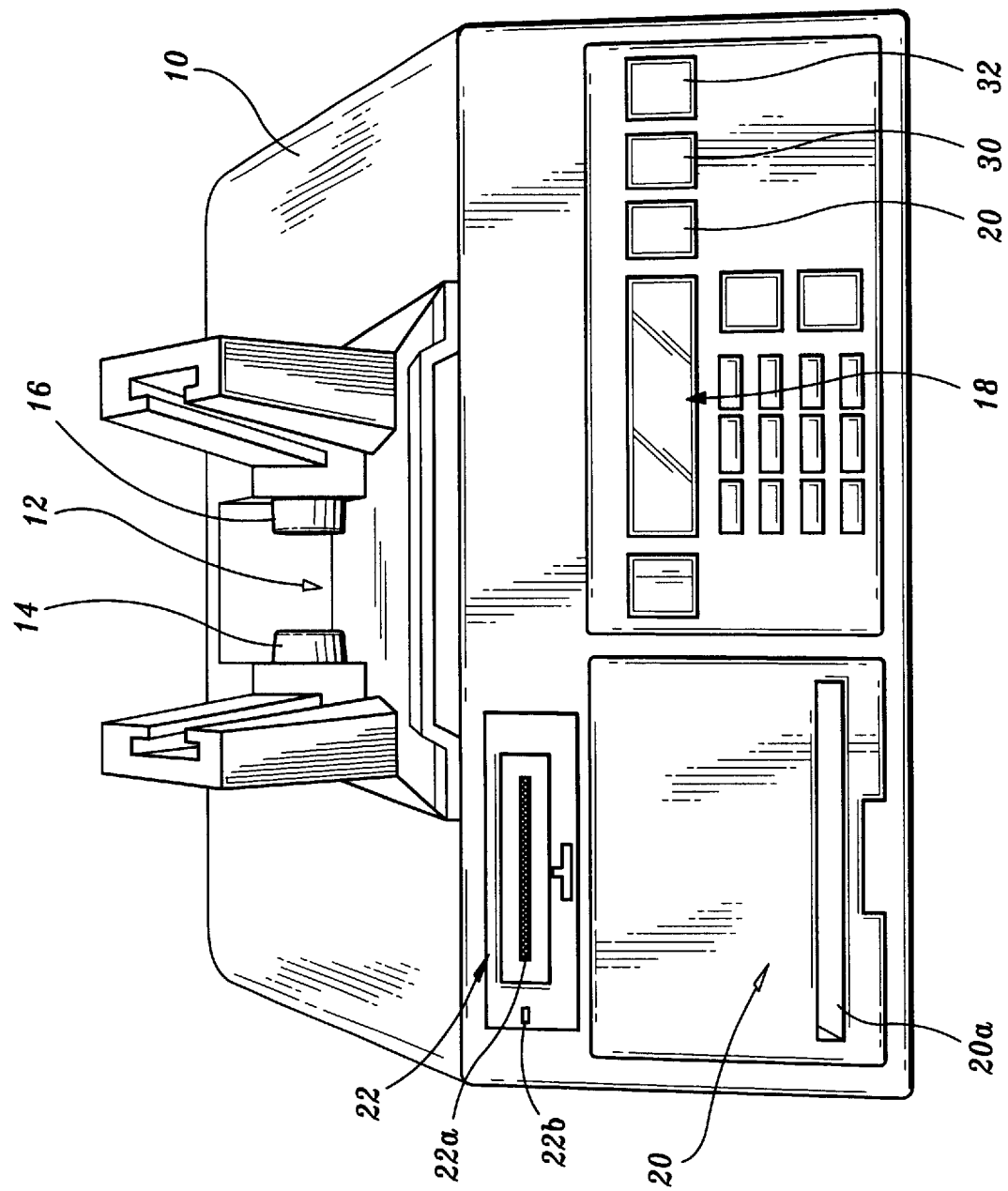
FIG. 1 is a perspective view of an ultrasound bone sonometer incorporating a card reader and an associated LED display.
Figure 2:
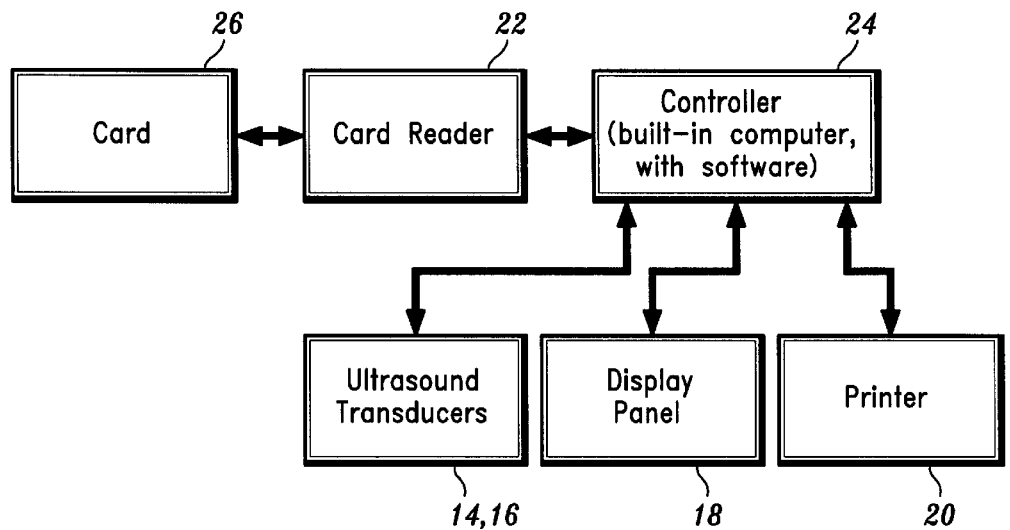
FIG. 2 is a block diagram illustrating interconnections between subsystems of the bone sonometer of FIG. 1.

Referring to FIGS. 1 and 2, an ultrasound bone sonometer 10 includes a foot well 12 adapted to receive the heel of a patient's foot, or a test object (phantom), between a pair of ultrasound transducers 14 and 16 so that ultrasound measurements can be made of the calcaneus (heel bone), or of the phantom, using ultrasound energy sent from one to the other of transducers 14 and 16 through the heel or the phantom. For a patient examination, typically the patient is seated and a foot positioning aid ensures proper orientation and positioning of the patient's foot. Sonometer 10 is a "dry" system in that it does not require the patient's heel to be inserted in a liquid (water) bath for acoustic coupling with the transducers, although the charging arrangement discussed herein can be applied to "wet" systems as well. A controller 24, comprising a built-in computer and its software, controls the examination procedure in which transducers 14 and 16 first move together into acoustic coupling with each other for an initial ultrasound measurement, then move apart to allow a patient's heel to be placed between them, then move toward each other and into engagement with the patient's heel at a controlled pressure to ensure a good acoustic coupling. Controller 24 then commands one transducer to send ultrasound energy to the other through the patient's heel. Controller 24 processes information derived from ultrasound energy received at the receiving transducer when the transducers are acoustically coupled with each other and when they are acoustically couplet with the patient's heel, together with other information, to produce estimates of bone characteristics and display results. Each transducer is capped with a soft elastomer pad acoustically coupled with the actual transducing element. An ultrasound coupling gel is used to help acoustically couple the pads to the patient's heel.

A patient examination typically measures speed of sound (SOS) and broadband ultrasound attenuation (BUA). Measuring SOS involves measuring the transit time of ultrasound energy and knowing or measuring a relevant distance, as well as using other information. Measuring BUA involves an analysis of the received ultrasound energy and other information to determine differences in attenuation within different frequency bands. The built-in computer and software serving as controller 24 use the measured or estimated SOS and BUA parameters to calculate a third parameter called Quantitative Ultrasound Index (QUI), sometimes called "stiffness," which combines SOS and BUA information. Based on the QUI/stiffness value, the built-in computer and software estimate a Bone Mineral Density (BMD) value, and calculate T-scores. A T-score is based on comparing a patient's BMD results to a large database of young adults, matched by sex and ethnicity, in order to help classify the patient's risk of developing osteoporosis, using internationally accepted guidelines established by the World Health Organization. If desired, and if an external computer with suitable software and database is available, a Z-score can be derived as well, through a comparison of the patient's BMD results with a reference database of sex, age and ethnicity matched population, to serve as an estimate of the risk of future fracture. The bone sonometer has an alphanumeric screen display 18 to display examination results and other information, and LED (light emitting diode) indicator 22b, and an internal printer 20 providing a printout of examination results and other information through a slot 20a.

A card reader 22 is built-in and is coupled to controller 24. Card reader 22 is adapted to interact with a card 26 (FIG. 2) inserted therein through slot 22a by exchanging information therewith that includes validation information relating, e.g., to charges to the card for patient examinations.

For a patient examination, the operator turns on bone densitometer 10, e.g., by pressing a touch pad 28 labeled ON. LED 22b lights up to show that the machine is ON, and the machine carries out preliminary operations such as moving transducers 14 and 16 toward each other until they pads touch and are in acoustic coupling with each other, and transmitting ultrasound energy from one transducer to the other, measuring various parameters based on the received ultrasound energy and other factors, and storing appropriate information. The operator then presses a touch pad labeled OPEN/PREP. The machine moves transducers 14 and 16 away from each other, and the operator prepares for a patient examination by placing gel on the pads of transducers 14 and 16 to ensure acoustic coupling with the patient's heel, positioning the patient's foot in well 12 and securing the foot positioning aid and otherwise preparing for a patient examination. The measuring operation starts in response to the operator pressing a touch pad 32 labeled MEASURE. However, the machine will commence the patient examination in response to the MEASURE command only if at the time the operator presses touch pad 32, a valid card 26 is present in slot 22a of card reader 22. Card reader 22 reads information from card 26, supplies it to controller 24, and controller 24 determines if the card is valid. The information from card 26 includes data indicative of how many units remain on the card, where a unit corresponds to one patient examination. Assuming that a card 26 with at least one unit on it has been inserted in reader 22, controller 24 responds to the operator pressing touch pad 32 (MEASURE), to command reader 22 to change the card's contents to indicate that one unit had been charged to the card. Then, controller 24 proceeds to issue the appropriate commands to transducers 14 and 16 and to process information to complete the patient's examination and display and print the results, as in the Sahara unit currently available commercially from Hologic, Inc. If the patient examination is unsuccessful, controller 24 commands card reader 22 to restore card 26 to the number of units it had before being charged for the patient examination that failed. In alternative embodiments, the charging sequence can involve charging the card at some other time prior to completing the patient examination, but still removing the charge from the card if the patient examination is not successfully concluded. In a current embodiment, card 26 includes a counter loaded with a number of units representing the number of prepaid patient examinations.

Thus, in a current embodiment bone sonometer 10 responds normally to operator commands ON, OPEN and PREP whether or not a card 26 has been inserted in card reader 22, and whether or not the card is valid or its counter is empty or not. However, bone sonometer 10 does not respond to a MEASURE command from the operator to carry out a patient examination unless a valid card had been inserted in card reader 22 and the card reader had deducted a unit from the counter on the card representing the number of prepaid patient examinations. If the prepaid units stored in card 26 have been used up before the card is inserted in reader 22, bone sonometer 10 will not respond to a MEASURE command from the operator for a patient examination. Only after card reader 22 deducts a unit from the appropriate counter on card 26 will sonometer 10 carry out the patient examination. If the patient examination is not successful, card reader restores the unit in the card counter so that no net charges are made to the card for unsuccessful patient examinations. If there is no card 26 in card reader 22, sonometer 10 works normally in response to ON, OPEN and PREP commands entered through touch pads 28 and 30, but does not respond to a MEASURE command entered through touch pad 32. The same result obtains if there is a card in reader 22 but the card is not a valid card, e.g., has no remaining units that can be charged for a patient's examination. If at any time before pushing pad 30 for the MEASURE command the user inserts into card reader 22 a valid card 26, with at least one unit remaining in the relevant counter, sonometer 10 responds normally to pushing the MEASURE command and proceeds with the patient examination after deducting a unit from card 26. The same result obtains if the user inserts a valid card 26 into card reader after having tried pushing in the MEASURE command before having a valid card in reader 22—once a valid card is in reader 22, the system responds normally to the MEASURE command and decrements the relevant counter in card 26. If desired, card 26 can be encoded with information related to an expiration date or a life span. In that case, controller 24 will accept as valid only a card 26 that has not expired.

Bone sonometer 10 provides a reminder to users when card 26 gets low in available units. While the reminder can take different forms, in a current embodiment a light emitting diode 22b visible at the front panel of densitometer 10, near card slot 22a, is normally ON for as long as sonometer 10 remains ON but blinks (goes OFF) to indicate with increasing insistence that the card is getting low in available units. For example, LED 22b does not blink when a card 26 with 11 or more units is in card reader 22, but blinks once if card with 10 remaining units is in and card reader decrements it to 9 units, twice when reader 22 decrements the card from 9 to 8 units, and so on, and blinks 10 times if a card with only one remaining unit is charged (so that no more units remain for future patient's examinations). An additional factor that helps alert the user's attention is that the response to the MEASURE command is delayed by approximately half a second per blink of LED 22b. Other reminders are contemplated—for example a message at display 18 that can include information as to the number or remaining units, an audible reminder, or some other way to communicate to a user that the card will soon need to be replaced or rejuvenated.

If a user has inserted a valid card 26 in reader 22 before pushing the MEASURE pad 32 but pulls it out of reader 22 immediately after pushing the MEASURE pad 32, the card will be charged for a patient examination but sonometer 10 will abort the examination due a detected absence of a valid card from reader 22 during the MEASURE procedure. A user can start a new examination with the same card, but the card will be charged for the new examination in the normal manner, as described above, and the point deducted for the aborted examination will not be restored.

For certain procedures that can be similar or even identical to a patient examination from the machine's point of view, sonometer 10 does not require the use of a valid card 26. For example, sonometer 10 does not require a card to carry out a procedure using a calibration object called a phantom that has known bone characteristics, placed between transducers 14 and 16 as a patient's heel would be placed for a patient examination. While alternative implementations are contemplated, in a current embodiment the user initializes the system twice, by pushing the ON pad 28 twice. In response, display 18 shows a message to the effect that the system is in a Quality Control (QC) mode. In this mode, a user proceeds with the normal calibration procedure used in the Sahara bone densitometer from Hologic. Inc., and can obtain SOS and BUA measurement or estimates, but not BMD or QUI estimates or printouts. In alternative embodiments, a QC mode can be entered in other ways, for example through a special QC command or some other command. A calibration procedure can show at display 18 the values of parameters such as QAB and QAS, where QAB is a dimensionless quantity calculated by dividing the BUA measured in the calibration procedure using the phantom by a value that was entered into controller 24 at the manufacturing facility and also appears on a label secured to the phantom, and QAS also is a dimensionless quantity and is calculated by dividing the SOS measured in the calibration procedure using the phantom by the phantom SOS value measured at the manufacturing facility and stored in controller 24 and also printed on a label secured to the phantom. The calibration results can be printed at printer 20.

Special cards can be provided to service personnel to carry out various procedures, including patient examinations, calibrations, testing, maintenance, upgrading, etc,, without charging the densitometer user.

In a current embodiment of the system disclosed herein, card 26 is a smart card commercially available under the trade name Braincard from Braincon Technologies in Vienna, Austria, and card reader 22 is a smart card reader commercially available from the same source under the trade name Braincard Universal Reader BC0103. Card reader 22 includes a processor such as AT89C52bzw and/or DS80C320, and memory such as 128K RAM memory, a power supply and an interface such as RS232, $I^2C$, and OMRON. Card reader 22 is compatible with a standard known as PC/SC and can read from or write into or onto a card such as a contact memory or a CPU card or a contactless card such as those commercially available under the trade names MIFARE and LOGIC.

Figure 3:
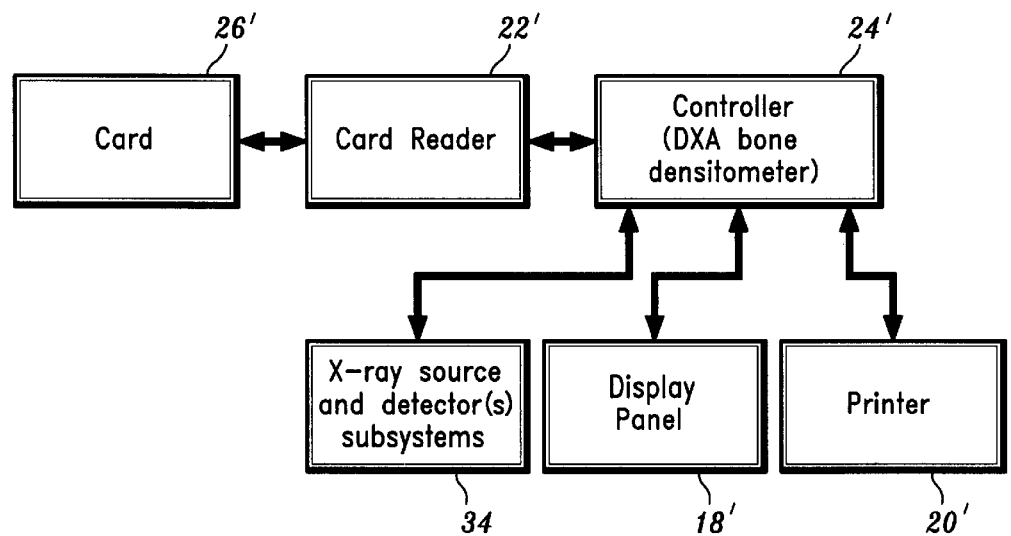
FIG. 3 is a block diagram illustrating an x-ray bone densitometer with a card reader.

In a DXA bone densitometer, a similar arrangement for charging is used as illustrated in block diagram form in FIG. 3. A card reader 22' exchanges information with a card 26' and a suitably programmed computer serves as a controller 24' for the machine functions. In a manner analogous to that discussed for sonometer 10 above, the DXA bone densitometer permits a patient examination only when card 26' is charged as discussed above, but carries out calibrations and QC procedures such as those involving sending x-rays through a calibration phantom and processing outputs from x-ray detectors, without charging card 26'. Again, service personnel can be provided with similar special cards. In the case of DXA there are different types of patient examinations, such as hip, whole body, lateral, etc. The charge can be the same for each type or, in an alternative embodiment, different charges can be made to the card for different procedures. For example, a look-up table can be stored in controller 24' responding to the operator's request for a particular procedure to command card reader 22' to deduct an appropriate charge from card 26' that can be different for different procedures. Controller 24' commands the operation of x-ray and detector subsystems 34, and the operation of display 18' and printer 20' in a manner analogous to the way controller 24 command the operations of the transducers, display and printer in bone sonometer 10.

Figure 4:
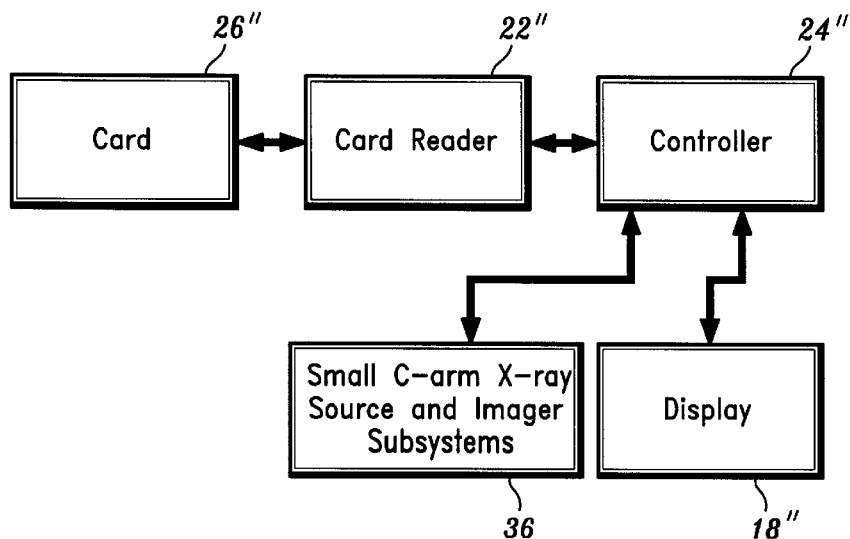
FIG. 4 is a block diagram illustrating a small C-arm fluoroscope unit with a card reader and bone densitometry capabilities.

In a small C-arm, another similar arrangement is used as illustrated in FIG. 4, in which a card reader 22" exchanges information with a card 26". Upon validation and, if desired charging, a card in a manner analogous to that discussed in connection with FIGS. 1 and 2, controller 24" permits a patient examination in which a body part is x-rayed for imaging or for bone densitometry, and controls a subsystem 36 which comprises the small C-arm x-ray source and imaging equipment. In case of using the C-arm for densitometry, the operation is analogous to that for sonometer 10, in that controller 24" permits a patient examination when a valid card is charged but permits a calibration or QC procedure without charging the card, and permits a special service personnel card to be used for all types of examinations. In case of operating the small C-arm for fluoroscopy, card 26" stores and exchanges with card reader 22" information related to x-ray dosage. In particular, card 26" typically is unique to an individual user, and stores information related to x-ray dosage for that individual for a relevant time period, such as the number of hours the individual has worked at that C-arm or similar C-arm units in a time period, or the number of units of dosage that the individual has accumulated when so using the card. If desired, the system can be set up not to charge card 26" for use of the small arm for fluoroscopy, but to require the presence of a valid card in reader 22" in order to permit fluoroscopy, so as to ensure that x-ray dosage information will be collected. Alternatively, fluoroscopy usage can be allowed without the presence of a valid card in reader 22".

Figure 5:
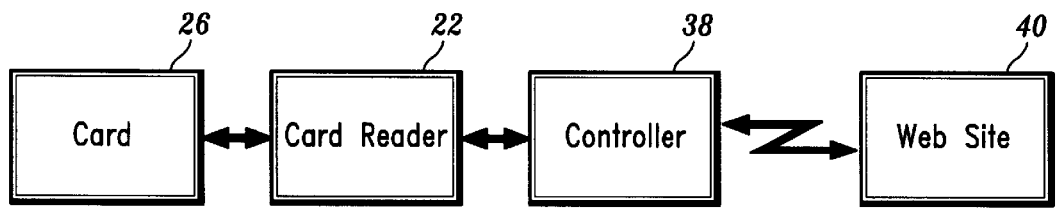
FIG. 5 is a block diagram illustrating rejuvenation of cards via a communication link.

When the card is of the type that can be rejuvenated, e.g., by adding units that would authorize additional patient examinations, a system such as illustrated in FIG. 5 can be used. The system comprises a card reader 22 that can be the same or similar to those discussed above, and a controller 38 that differs from the controllers discussed above only in that it has provisions for interacting with a communication link such as the Internet to connect to a remote source, such as a Web Site 40. For example, controller 38 can include provisions for interacting with a desktop computer at the same premises, connected to controller 38 via a Local Area Network (LAN) for example, to exchange information therewith, and the desktop computer in turn can have conventional provisions for Internet communications. Web site 40 can a site maintained by of for the manufacturer of the diagnostic equipment, or by or for a third party. In operation, a card user inserts a card 26 into reader 22, establishes a connection to Web site 40 via controller 38, and requests, e.g., the addition of a certain number of units to card 26. The user can have an account at Web site 40, in which case the account is appropriately charged, and Web site 40 sends command information to controller 39 and therethrough to card reader 22 to change the information on card 26 appropriately. Alternatively, Web site 40 can require the user to provide information needed to charge a third party's credit, debit or some other type of charge card for the units to be added to card 26, in which case the charge for the new units is made as required by the procedures established for the third party's card, and card 26 has its information content changed to reflect the addition of units. Suitable passwords and encryption can be employed to ensure transaction security, as is known in current financial transactions over links such as the Internet. Alternatively, a card 26 can be rejuvenated locally, without the use of a communication link, by using a properly controlled or authorized card reader 22 that has the added capability of altering the information on the card so as to add units for additional patient examinations.

If the bone sonometer or densitometer is connected or connectable to a remote location that can transmit authorization for patient information, e.g., via an Internet connection, information authorizing one or a number of patient examinations or a permitted time period for patient examinations, can be provided directly, without the need for cards or card readers. For example, the user can have an account with a central location and this account can be charged upon a request that the user transmits over the communication link, or a user's credit or debit or some other card, or some other financial instrument or account of the user can be charged. Other ways of achieving a charge-peruse for some uses but not for other uses of the diagnostic equipment can be implemented within the spirit of the disclosure in this patent specification. As one example, through accessing a remote location via a communication link such as the Internet, the user can arrange for a payment for a specified number or patient examinations, or a specified time period, or some combination of the two, and the agreed on authorization can be stored in controller 24 (or 24' or 24") so that the machine can carry out the authorized patient examination and keep track of usage, until using up the authorized number or unit and/or time. The payment in this case can be by charging an account the user has with the remote location or with a third party, by charging a credit or debit card, or in some other way.

What is claimed is:

1. An ultrasound bone sonometer or densitometer comprising:
   a foot well adapted to receive the heel of patient's foot;
   a sending ultrasound transducer and a receiving ultrasound transducer facing each other in the foot well;
   a controller coupled to the transducers to selectively carry out a patient examination by causing the sending transducer to send ultrasound energy toward the receiving transducers through a patient's heel positioned between the transducers and causing the receiving transducer to provide information related to ultrasound energy received thereby, and by processing said information to derive therefrom estimates of bone characteristics;
   a card reader coupled to said controller and adapted to exchange charge-related information with a card provided to the card reader;
   said controller being responsive to an operator request for a patient examination and to charge-related information supplied to the controller from the card reader to: (a) to determine if the card is valid; (b) carry out a patient examination upon a determination that the card is valid, and (c) cause the card reader to charge the card for the patient examination;
   said controller further being responsive to an operator request for a calibration or quality control procedure to carry out a calibration by causing the sending transducer to send ultrasound energy toward the receiving transducers through an object other than a patient's heel, said object being positioned between the transducers, and causing the receiving transducer to provide information related to ultrasound energy received thereby through said object, and by processing the last-recited information to derive calibration parameters therefrom, without making a charge to said card.

2. An ultrasound bone sonometer or densitometer as recited in claim 1, further comprising a soft elastomer pad capping each sending and receiving transducer.

3. An ultrasound bone sonometer or densitometer as recited in claim 2, wherein each soft elastomer pad is acoustically coupled to the sending and receiving transducer.

4. An ultrasound bone sonometer or densitometer as recited in claim 1, further comprising a mechanism for moving at least one of the sending and receiving transducers relative to the other.

5. An ultrasound bone sonometer or densitometer as recited in claim 1, wherein the charge-related information includes units and wherein the controller can determine how many available units remain on the card, the units providing validating information relating to charges to the card for patient examination.

6. An ultrasound bone sonometer or densitometer as recited in claim 5, wherein the controller deducts units from the card for a patient examination.

7. An ultrasound bone sonometer or densitometer as recited in claim 6, further comprising an indicator for providing an indication when the card gets low in available units.

8. An ultrasound bone sonometer or densitometer as recited in claim 7, wherein the indicator comprises a message display.

9. An ultrasound bone sonometer or densitometer as recited in claim 7, wherein the indicator comprises a light emitting diode (LED).

10. An ultrasound bone sonometer or densitometer as recited in claim 9, wherein the LED blinks to indicate with increasing insistence that the card is getting low in available units.

11. An ultrasound bone sonometer or densitometer as recited in claim 1, further comprising a communication link, wherein the controller can communicate with a remote source via the communication link for updating charge-related information on the card.

12. An ultrasound bone sonometer or densitometer as recited in claim 11, wherein the communication link comprises the Internet.

13. An ultrasound bone sonometer or densitometer as recited in claim 12, herein the controller interacts with a computer to exchange information therewith, the computer communicating with the Internet.

14. A bone sonometer or densitometer comprising:
   a support for a patient's body or a body part;
   a measurement subsystem and a controller coupled therewith to selectively carry out a patient examination in which energy is sent through the patient and information from said energy is processed to derive therefrom estimates of bone characteristics;
   a card reader coupled to said controller and adapted to exchange charge-related information with a card provided to the card reader;
   said controller: (a) being responsive to an operator request for a patient examination and to charge-related information supplied to the controller from the card reader to determine if the card is valid; (b) carrying out said patient examination upon a determination that the card is valid; and (c) causing the card reader to exchange with the card information indicative of a charge made to the card for said patient examination;
   said controller further being responsive to an operator request for a calibration or quality control procedure to carry out a calibration by causing energy to be sent through an inanimate object and information therefrom is processed to derive calibration parameters, without making a charge to said card.

15. A bone sonometer or densitometer as recited in claim 14, wherein the charge-related information includes units and wherein the controller can determine how many available units remain on the card, the units providing validating information relating to charges to the card for patient examination.

16. A bone sonometer or densitometer as recited in claim 15, wherein the controller deducts units from the card for a patient examination.

17. A bone sonometer or densitometer as recited in claim 16, further comprising an indicator for providing an indication when the card gets low in available units.

18. A bone sonometer or densitometer as recited in claim 17, wherein the indicator comprises a message display.

19. A bone sonometer or densitometer as recited in claim 17, wherein the indicator comprises a light emitting diode (LED).

20. A bone sonometer or densitometer as recited in claim 19, wherein the LED blinks to indicate with increasing insistence that the card is getting low in available units.

21. A bone sonometer or densitometer as recited in claim 2, further comprising a communication link, wherein the controller can communicate with a remote source via the communication link for updating charge-related information on the card.

22. A bone sonometer or densitometer as recited in claim 21, wherein the communication link comprises the Internet.

23. A bone sonometer or densitometer as recited in claim 22, wherein the controller interacts with a computer to exchange information therewith, the computer communicating with the Internet.

* * * * *

UNITED STATES PATENT AND TRADEMARK OFFICE
CERTIFICATE OF CORRECTION

PATENT NO. : 6,234,969 B1  Page 1 of 1
DATED : May 22, 2001
INVENTOR(S) : Chaintreuil et al.

It is certified that error appears in the above-identified patent and that said Letters Patent is hereby corrected as shown below:

<u>Title page,</u>
Item [75], please correct the spelling of the fifth named inventor, from "Daval Liuhar" to -- Davul Ljuhar --.

Signed and Sealed this

Thirteenth Day of November, 2001

Attest:

NICHOLAS P. GODICI
Attesting Officer  Acting Director of the United States Patent and Trademark Office